United States Patent
Spahlinger et al.

[11] Patent Number: 5,844,494
[45] Date of Patent: Dec. 1, 1998

[54] METHOD OF DIAGNOSING ERRORS IN THE PRODUCTION PROCESS OF A SYNTHETIC FILAMENT YARN

[75] Inventors: Jorg Spahlinger, Wernelskirchen; Manfred Mayer; Ulrich Enders, both of Remscheid; Bernd Neumann, Radevormwald, all of Germany

[73] Assignee: Barmag AG, Remscheid, Germany

[21] Appl. No.: 971,766

[22] Filed: Nov. 17, 1997

Related U.S. Application Data

[63] Continuation of Ser. No. 362,456, filed as PCT/EP94/01316 Apr. 26, 1994 published as WO94/25869 Nov. 10, 1994.

[30] Foreign Application Priority Data

| Apr. 29, 1993 | [DE] | Germany | 43 14 049.1 |
| Jun. 2, 1993 | [DE] | Germany | 43 20 424.4 |
| Jul. 30, 1993 | [DE] | Germany | 43 25 632.5 |
| Aug. 31, 1993 | [DE] | Germany | 43 29 213.5 |

[51] Int. Cl.$^6$ ..................................................... G08B 21/00
[52] U.S. Cl. ........................... 340/677; 340/511; 340/532; 57/264; 57/265
[58] Field of Search .................................... 340/677, 679, 340/522, 511; 65/377, 332, 382, 484, 491; 57/264, 265

[56] References Cited

U.S. PATENT DOCUMENTS

| 3,731,069 | 5/1973 | Goto et al. | 364/470.15 |
| 4,010,599 | 3/1977 | Luthi | 57/264 |
| 4,058,962 | 11/1977 | Spescha et al. | 57/265 |
| 4,720,702 | 1/1988 | Martens | 340/677 |
| 4,953,367 | 9/1990 | Memminger et al. | 66/132 R |
| 5,017,911 | 5/1991 | Muller et al. | 340/677 |
| 5,027,484 | 7/1991 | Baba | 28/185 |
| 5,207,763 | 5/1993 | Jacobsson | 66/163 |
| 5,469,149 | 11/1995 | Binner et al. | 65/377 |

FOREIGN PATENT DOCUMENTS

| 0 457 450 | of 0000 | European Pat. Off. . |
| 2 207 471 | of 0000 | European Pat. Off. . |

*Primary Examiner*—Thomas J. Mullen, Jr.
*Assistant Examiner*—Ashok Mannava
*Attorney, Agent, or Firm*—Bell Seltzer Intellectual Property Law Group of Alston & Bird LLP

[57] ABSTRACT

Method of diagnosing failures in a production process of a synthetic filament yarn, in which a first process parameter dependent on the process control is continuously measured and evaluated, and in which as a function of the evaluation or course derived therefrom an indication signal is generated, there being continuously measured and evaluated at least a second reference parameter dependent on the process control, and the indication signal being generated, when an error-typical behavior is found in the first and in at least one additional parameter.

9 Claims, 2 Drawing Sheets

METHOD OF DIAGNOSING ERRORS IN THE PRODUCTION PROCESS OF A SYNTHETIC FILAMENT YARN

This application is a continuation of copending application Ser. No. 08/362,456, filed as PCT/EP94/01316 Apr. 26, 1994, published as WO94/25869 Nov. 10, 1994, now abandoned.

BACKGROUND OF THE INVENTION

The present invention relates to a method of processing a continuous synthetic filament yarn while concurrently monitoring its quality.

EP 207 471 and corresponding U.S. Pat. No. 4,720,702 disclose a method of monitoring the quality of a yarn produced by a false twist crimping process. This method has shown that the yarn tension measured downstream of a friction false twist unit is surprisingly indicative of the quality of a produced yarn and of the produced package, when from the continuously measured value suitable indicative values are obtained—in the known case a mean value—and a suitable evaluation occurs. However, based on the knowledge obtained so far, this applies only to false twist crimping processes.

In other methods of producing a synthetic filament yarn, in particular in the spin process, high-speed spin process, draw spin process, as well as spin draw process, it has not been possible to find a similar expressiveness of the yarn tension. This results in particular from the greater complexity of such processes, in which many process parameters exert different effects on the yarn tension.

Likewise, other process parameters do no permit a comprehensive indication of the quality of the produced yarn and the produced package.

It is the object of this invention to obtain data by measuring in a continuous spinning process for a synthetic yarn, which are indicative of the quality of the produced yarn and the produced package. The data are therefore intended to permit an indication as to the quality of the product and/or the process control and process correction by a control or adjustment. Likewise—if need arises, even while accepting an inferior quality—it is intended to enable an early interruption of the production process and an avoidance of rejects.

SUMMARY OF THE INVENTION

The above and other objects and advantages of the present invention are achieved by the provision of a processing method for continuous synthetic filaments as described and claimed herein.

Besides the actual diagnosis of errors, the error diagnosis is understood to further include the monitoring and control of the process which are carried out on the basis of an error diagnosis. In their broadest meaning, "errors" are understood to include any deviations from normal process and yarn parameters.

To summarize, in the method of the present invention, a first process parameter dependent on the process control is continuously measured. The thus obtained course of measured values is continuously evaluated, and an indication signal is generated as a function of this evaluation, or of a course derived from the course of the measured values. Furthermore, at least a second process parameter dependent on the process control is likewise continuously measured and evaluated. When in the case of the first and at least one further process parameter an error-typical behavior is found, an indication signal will be generated. The first and at least the second process parameter may be dependent on one another. An error in the here defined sense will disturb this dependency, which forms the basis for a detection. The first and at least the second process parameter may also be independent of one another. An error may upset this independence, i.e., the error forming the basis for detection, will become noticeable in a simultaneous change of both process parameters. Certain errors lead to typical changes of the at least two process parameters, i.e., the process parameters exhibit an error-typical behavior.

In a first embodiment of this invention, at least two process parameters are simultaneously compared or chronologically correlated during the process, and an indication signal is generated, when the error-typical behavior points to a deviation from the normal course of the process.

In a further embodiment of the method in accordance with the invention at least the two process parameters are linked. Should this linkage be indicative of an error-typical behavior with respect to the normal course of the process, an indication signal is generated on the basis thereof.

The method can be employed in particular in the spinning of a synthetic filament yarn. In this process, the takeup speed may be higher than 2,000 meters per minute, and the yarn may be withdrawn by the takeup system directly from the spinneret. In this manner a preoriented yarn (POY) is produced. To produce a POY yarn it is also possible to interpose a godet. A further increase of the takeup speed also allows to realize a full orientation, in particular by interposing a heating system, so that a fully oriented yarn is produced. On the other hand, it is also possible to include in the process a godet, which withdraws the yarn from the spinneret, or a draw zone consisting of one or more godets. Departing from previous monitoring methods, a one-dimensional monitoring by evaluating only one parameter is abandoned. Rather, at least two parameters are evaluated, and insofar a quasi two- or multi-dimensional observation of the process is performed, in that the results of the observation with respect to the two or more parameters are, for example, compared again simultaneously, or chronologically correlated and/or interconnected, and that the failure signal is obtained from the interconnection.

Process parameters and reference parameters include all variables, which can be measured continuously or intermittently from time to time on the advancing yarn (yarn temperature, yarn tensile force=yarn tension, yarn speed), on the package being formed (diameter, weight, bulging of front ends=deviation from the ideal-cylindrical shape), or on machine parts which define the process (rotational speeds, speeds, temperatures, torque pickup).

It is obvious that not all changes in the process parameters have an effect on the yarn quality. To enhance the expressiveness of the combined observation, it will be especially advantageous and useful to first determine, by experience (controlled preliminary tests with artificially generated deviations from the process and crisis situations), courses of critical points for each of the parameters. Courses of critical points are described as the courses of each parameter, which are symptomatic of certain process failures or product defects. They may include absolute values, extreme values of the continuously measured value of the respective parameter, the variation with time, the first or second derivative of the measured values of the respective parameter, the standard deviation or any other variable derived from the respective parameter, which is indicative of the error. In particular, it is possible to store characteristic courses of at least one of the described variables in a memory as an error mask. Different defects, for example, fluffs or knots in the yarn, may be generated artificially, it being possible to accurately register their effect on the observed parameters, in particular the yarn tension, and to store it as a corresponding error mask. To this end, one may also refer to Applicant's own, not yet published Application DE-A 43 14 049.1.

Parameters to consider include in particular the yarn tension, the package weight, the yarn thickness, the yarn temperature, or even any other adjustment parameter, such as, for example, spin head pressure, pump speed, spin head temperature, godet speed, and godet temperature. Suitable reference parameters include in particular also the programmed adjustment parameters, when no constant course of these adjustment parameters has been predetermined. To consider for such a programmed parameter are in particular the traversing motion and the traversing speed, which have a decisive influence on the course of the yarn tension measured in the takeup zone. In all these instances, it will be necessary to correlate the measured values or the variables derived therefrom, which initially differ already from one another by their dimension, and to determine their interdependence. This becomes unnecessary in cases where a similar parameter, for example, the yarn tension is measured at different points of the spinning process, for example within the draw zone between two godets, on the one hand, and in the takeup zone on the other.

BRIEF DESCRIPTION OF THE DRAWINGS

Some of the objects and advantages having been stated, others will appear as the description proceeds, when considered in conjunction with the accompanying drawings, in which.

In the drawing.

DETAILED DESCRIPTION OF THE PREFERRED EMBODIMENT

Figure 1:
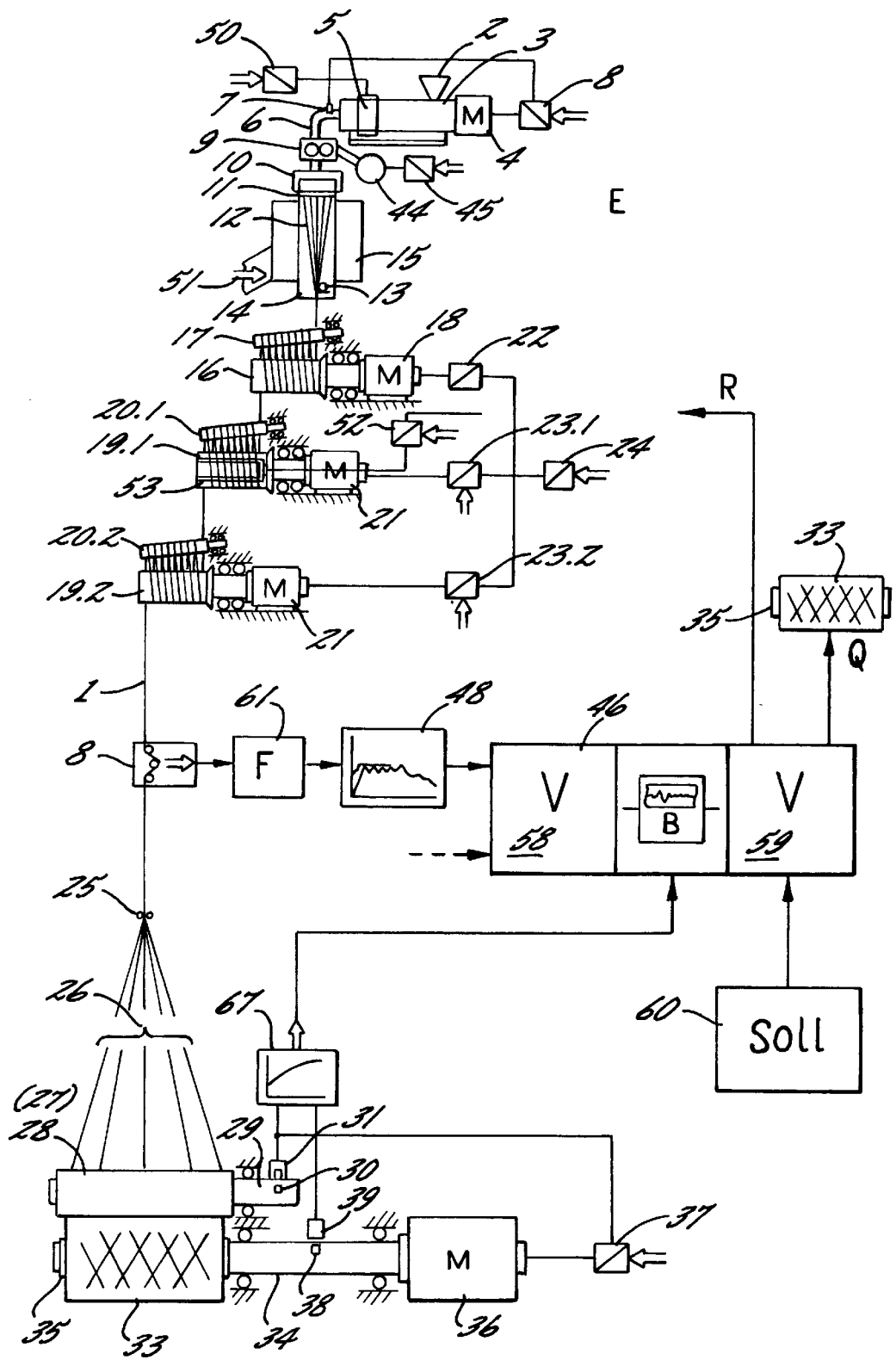
FIG. 1 is a schematic view of the process sequence, namely a spin process for producing and drawing a synthetic filament yarn, which employs one the embodiments.

The spin process includes the spinning of a yarn 1 of a thermoplastic material. The latter is supplied through a feed hopper 2 to an extruder 3. A motor 4 drives the extruder 3. The motor 4 is activated by a motor control unit 8. In the extruder the thermoplastic material is melted. To this end, use is made of the deformation work which is applied by the extruder to the material. In addition, a heating device 5 in the form of a resistance heater is provided which is activated by a heating control unit 50. Through a melt line 6 which may be provided with a pressure sensor 7, the melt advances to a gear pump 9, which is driven by a pump motor 44. The latter is activated by a pump control unit 45, so as to permit a very fine adjustment of the pump speed. Pump 9 advances the melt flow to a heated spin box 10, the underside of which accommodates a spinneret 11. From spinneret 11, the melt exits in the form of fine filaments 12. The filaments advance through a quench chamber 14. In the quench chamber 14 an air current is directed by blowing 15 transversely or radially to the sheet of filaments, thereby cooling the filaments.

At the outlet end of quench chamber 13, the sheet of filaments is combined by a spin finish application roll 13 to a yarn 1 and provided with a spin finish fluid. A godet 16 withdraws the yarn from the quench chamber and the spinneret. The yarn loops several times about godet 16. To this end, a guide roll 17 is used which is arranged axially inclined with respect to godet 16. Guide roll 17 is freely rotatable. Godet 16 is driven at a preadjustable speed by a motor 18 and a frequency device 22. This drawoff speed is by a multiple higher than the natural speed at which the filaments exits from spinneret 11.

Subjacent godet 16 is a pair of draw rolls or godets 19.1 and 19.2 with a further guide roll 20.1 and 20.2. In their arrangement, both correspond to that of godet 16 with guide roll 17. For the drive of draw rolls 19.1 and 19.2 motors 21.1 and 21.2 with frequency control devices 23.1 and 23.2 are used. The input frequency of frequency control devices 22, 23.1, and 23.2 is uniformly predetermined by a controllable frequency control device 24. In this manner, it is possible to individually adjust on frequency devices 22, 23.1, and 23.2 the speed of godet 16, and draw rolls 19.1 and 19.2, respectively. The speed level of godet 16 and draw rolls 19.1, 19.2 is however adjusted collectively on frequency device 24.

The first draw roll 19.1 is provided with a heating system 53, which allows to heat the surface of the roll and accordingly the yarn, so as to permit to influence to a great extent the yarn properties obtained by the draw process. The temperature of heating system 53 is controllable by a control unit 52.

From the last draw roll 19.2, the yarn 1 advances to a so-called "apex yarn guide" 25, and thence into a traversing triangle 26. Only FIG. 2 shows a yarn traversing mechanism 27 in the form of a cross-spiralled roll and a yarn guide reciprocating therein, which traverses the yarn over the length of a package 33 (traversing stroke, double stroke). In so doing, downstream of yarn traversing mechanism 27, the yarn loops about a contact roll 28 which is shown only in FIG. 1. Contact roll 28 rests against the surface of package 33, and serves for measuring the surface speed of package 33. The package 33 is formed on a tube 35. The tube 35 is clamped on a winding spindle 34. A spindle motor 36 and spindle control unit 37 drive winding spindle 34 such that the surface speed of package 33 remains constant. As a result, the spindle speed decreases hyperbolically in the course of the winding cycle. To keep the surface speed of package 33 constant, the speed of freely rotatable contact roll 28 is sensed on the shaft of the contact roll by means of a ferromagnetic insert and a magnetic pulse generator, and spindle motor 36 is controlled as a function of the output signal of the pulse generator.

Yarn traversing mechanism 27 is driven by a motor 56, which is controlled by a control unit 57 (FIG. 2).

Arranged in the yarn path downstream of the second draw roll 19.2 is a yarn tension sensor (yarn tensiometer) 8, which allows to generate a signal representing the yarn tension. The signal emitted by the yarn tension sensor is still smoothed before being supplied to a computer. To this end, the output signal passes first supplied through a filter 61. In filter 61, periodical changes in the yarn tension, which correspond in their frequency to the traversing frequency, are smoothed. Therefore, in the output device, only such changes appear which are caused by other short-term occurrences of a high frequency. In the thus smoothed course of the yarn tension, however, only such yarn tension fluctuations still enter, which are based on a change in the traversing speed. Changes in the yarn tension are also caused by the traversing motion per se, i.e., in that the yarn is traversed along the package. In so doing, the yarn path between apex yarn guide 25 and the yarn traversing mechanism lengthens or shortens periodically with the consequence of a corresponding change in the yarn tension. These changes in the yarn tension have the same frequency as the traversing motion. The traversing frequency is predetermined by the number of double strokes (one forward and return movement of the traversing yarn guide) per unit time. Standard values range from 500 to 1500 double strokes per minute. It is possible to likewise eliminate the influencing of the yarn tension signal by these short-timed fluctuations, in that the output signal of yarn tensiometer 8 is passed through filter 61. This filter contains standard electronic components, which effect the desired, if possible, adjustable smoothing of the output signal. A suitable adjustment of this filter is accomplished in that also such changes in the yarn tension, which occur along with the traversing frequency, are eliminated and converted to a mean value. However, when using the invention, it is likewise possible as an alternative to compare these yarn tension fluctuations with a stored input of the traversing frequency, and to further evaluate only the difference signal as a reference signal (as is described further below). With its high-frequency components having been suppressed, the signal is then supplied to the yarn tension output device.

In device 48, the continuously measured yarn tension is output as a graphic record (yarn tension graph). The output signal of device 48 is input in a computer unit 46. In computer 46, the yarn tension graph may be stored for the entire winding cycle or important—selected—portions thereof. At the same time, the yarn tension signal is being processed in a manner, which is subject matter of this application and of embodiments described further below.

For all embodiments, the computer setup is illustrated identically in both Figures. The computer comprises a comparison unit 58. In one embodiment of the invention, the task of this comparison unit is to correlate the traversing speed of traversing law memory 47 and the yarn tension signal of yarn tension output device 48. This allows to determine, to which extent the course of the yarn tension is dependent on the course of the traversing speed. Of interest are in particular the chronological variations in the traversing speed. Both the amount of the variation and the speed of the variation, i.e., the variation derived as a function of time have an influence on the yarn tension. Previously determined conversion factors allow to convert the pattern of the traversing speed into a hypothetical tension, as it would be caused by a change in the traversing speed. As aforesaid, it is also possible to include in this hypothetical course of the tension the variations as they result from the traversing motion itself. The determination of the conversion factors is described further below. In any event, the hypothetical value of the yarn tension as derived from the traversing speed is deducted from the actual value of the yarn tension. The difference signal then indicates the changes in the yarn tension, which have not been caused by the change in the traversing speed and the traversing motion. Within the scope of this application, this yarn tension signal is indicated by the reference signal B. The described generation of the reference signal also occurs in the embodiment of FIG. 2, but is not shown therein. It should be explicitly stated that this reference signal, which is correlated with the traversing, corresponds already to the requirements of this invention for a multidimensional monitoring of the quality, and is suitable for evaluation. In the following, other observational dimensions are described. It should be remarked that these further observational dimensions may also be applied directly to the yarn tension signal 48, and lead to a similar increase in expressiveness of this yarn tension signal. The here described reference to the predetermined law of traversing allows, however, to obtain a fine tuning of the indication.

The reference signal B is input in a further comparison unit 66 of computer 46. In this comparison unit, the reference signal as obtained from the yarn tension, on the one hand, is possibly further processed to a variable derived therefrom, such as, for example, the mean value, the first or second derivative (variation with the time), the standard deviation, the roughness of the course of the signal, or the like. On the other hand, the reference value or the variable derived therefrom is compared with a further parameter. Basically to consider here are a process parameter and/or a product parameter.

Figure 2:
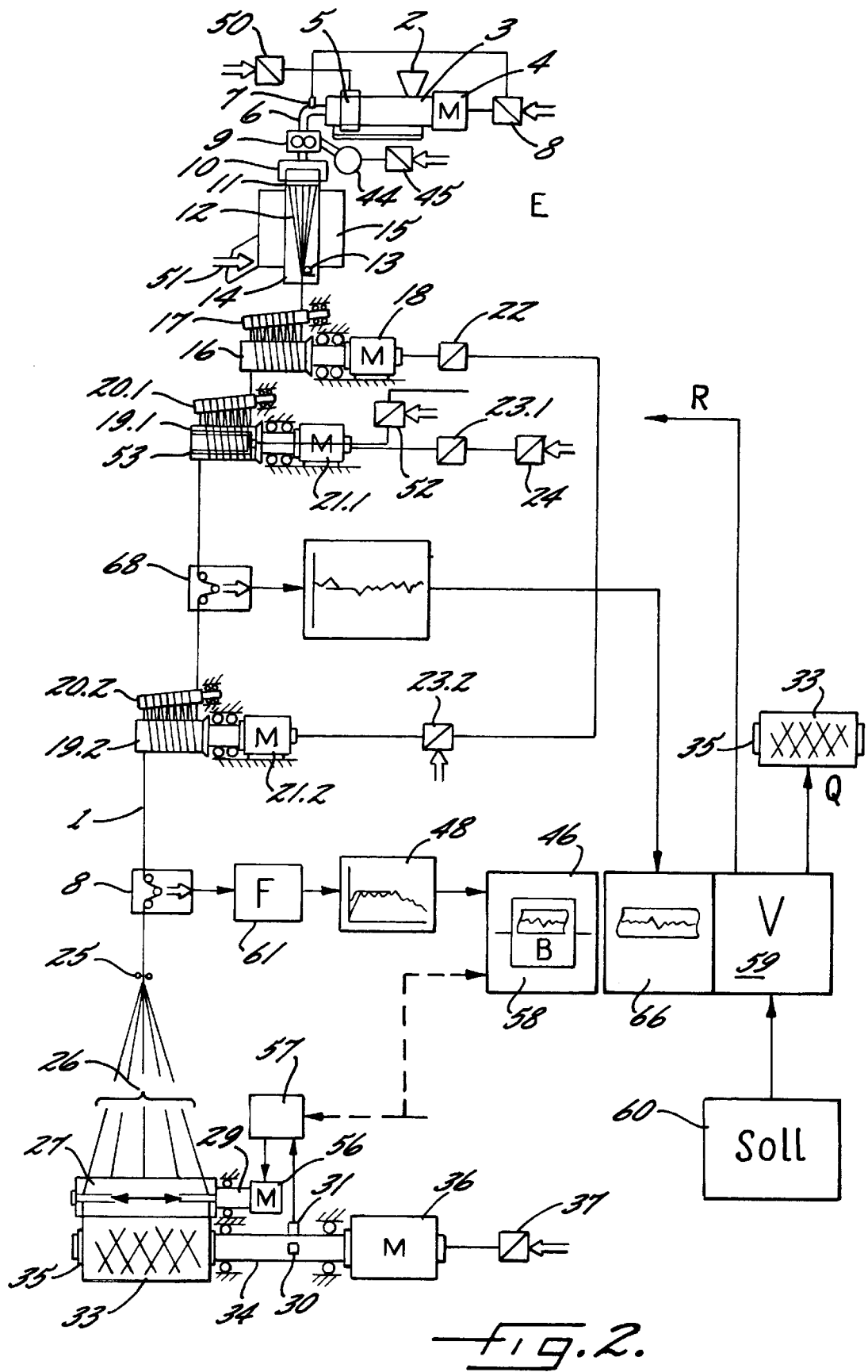
FIG. 2 is another embodiment of the invention to which the description of Figure applies in like manner.

In FIG. 1, as a further parameter of state, the diameter of package 33, or a variable derived from the diameter, is continuously measured. Also the weight may be considered for use as such a variable. However, connected therewith are factors of disturbance, such as the density of the wind, incorporated air, crossing angle, or the like. Consequently, it is not possible to consider the determined weight as an absolute value. To measure the diameter, the speed of spindle 34, and the speed of contact roll 28, which lies against the surface of the package, are measured. To this end, use is made of ferromagnetic inserts 30, 38 in both spindle 34 and contact roll 28, as well as corresponding pulse generators 31, 39. Whereas the speed of contact roll 28 serves simultaneously as a control variable for the adjustment of spindle motor 36 via spindle control unit 37 (see above), the speed of spindle 34 is also used—as is already referred in connection with FIG. 2—for the control of yarn traversing mechanism 27. In addition, however, both signals are converted into diameter D. To this end, a computer unit 67 is used, which receives both signals. The diameter signal is then input in comparison unit 66. As an alternative, it is also possible to derive from the diameter signal a further signal, which is input in comparison unit 66 in the place of the diameter signal or in addition thereto. Considered as such a derived signal is in particular the square of the diameter or the first mathematical derivative from the square of the diameter. Since the yarn speed is constant, this derivative must likewise be a constant. The first derivative is proportional to the advanced quantity of yarn. Deviations therefore suggest a disturbance of the process. When it is found in comparison unit 66, that these deviations coincide with disturbances in the yarn tension, it is possible to draw important conclusions as to the process control and the product, be it the yarn or the package wound therefrom.

Thus, a comparison of two parameters of state occurs in comparison unit 66, the word "comparison" being understood in its broadest meaning. It may be the formation of a difference. In so doing, it is necessary to first establish a uniform magnitude for both parameters. The comparison may also be in the non-mathematical meaning. Thus, in the case of both signals it is possible to determine courses of critical points, for example, extreme values, and to ascertain whether the extreme values of both parameters coincide in time, or whether there is at least a chronological connection between them. If such a chronological connection results, same will allow to draw a conclusion as to certain errors. Likewise however, the contrary may apply, i.e., should courses of critical points result in the case of only one of these variables, same may be indicative of certain errors or causes therefor.

Likewise, it is possible to correlate the parameters after a certain weighting.

Finally, the output signal of comparison unit 66 is input in a further comparison unit 59. In this comparison unit a comparison with a desired value may occur, which is predetermined by set-point input element 60. From this comparison, the quality signal is generated and output by the computer.

The quality signals Q, which, as described above, have been generated, are further processed as follows: the quality signal may be an optical or acoustical alarm or be emitted a graphic record. The latter is used to mark and classify the produced package.

The output signals of computer 46 may be used in particular as a control variable for controlling an adjustment parameter of the spin and draw processes. However, it is also possible to use the output signals of computer 46 for a quality identification of the finished packages, which are produced by the process.

To this end, the set-point input element is used to establish both tolerance values for the reference value or variables derived therefrom and error limits, which allow to judge whether or not to rate the quality of a package A, or B, or as reject.

However, the quality signal Q may also be used only as an alarm signal, for example, for interrupting the process and preventing a waste production.

As an alternative or in addition, the quality signal may be input, in particular, in one or more of the control devices

| | |
|---|---|
| 22 | for draw godet 16; and/or |
| 23.1, 23.2 | for the second draw godet 19.1, and/or |
| 19.2 | for influencing the draw process; |
| 24 | for controlling the drawoff speed; |
| 45 | for controlling the pump speed; |
| 49 | for controlling the extruder speed; |
| 50 | for controlling the heating device; |
| 51 | for controlling the cooling device (velocity of air flow); |
| 37 | for controlling the takeup speed; |
| 52 | for controlling the godet heating; and |
| 45 | for controlling the pump of the metering device. |

The extruder control unit is activated in particular when no metering pump 9 is used. In this instance, the extruder acts as a pump, and the activation of the extruder control unit, i.e., the speed of the extruder, allows to influence the output of the extruder.

When a metering pump 9 is used, it will be possible to influence the quantity of melt put through spin head 10 and spinneret 11 by activating pump control unit 45, i.e., the speed of metering pump 9.

The activation of cooling air control unit 51 allows to influence the cooling. This becomes effective especially on the yarn denier. In particular, it is also possible to influence the uniformity of the individual filaments with the use of special cooling devices, which allow to cool the filament sheets and/or the spinneret in sections.

In the embodiments of FIGS. 1 and 2 individual components are possibly exchangeable. Accordingly different parameters will be controlled in this instance. In particular, it is possible to replace the extruder with a discharge pump, and there also exist various other possibilities for cooling the sheet of filaments. Likewise, a further heating device may be provided in, or in the place of the draw systems.

The current high-speed spinning processes allow to also omit the drawing by godets. In this instance, the yarn is withdrawn from the spinneret by a single godet, and advanced to the winding head, or it is withdrawn from the spinneret directly by the takeup device. On the other hand, the draw process may also be replaced or supplemented with further elements, such as, an additional heating device, in particular a tubular heater.

The activation of the drawoff control unit 24 allows to influence the speed of godet 16 and godets 19.1 and 19.2, without changing the speed ratio. In this instance, the draw ratio remains constant, whereas the speed of the yarn is changed, thereby influencing its denier.

The activation of draw roll control unit 23.1 or 23.2 allows to influence the speed ratio between godets 19.1/19.2/16, and to thus change the draw ratio. The change in the draw ratio allows to vary not only the physical properties, but also the denier of the yarn.

Finally, the spindle control unit allows to also control by means of the quality parameter the circumferential speed of package 33, which is controlled by contact roll 28. This allows to influence in particular the package buildup and the yarn tension, under which the yarn is deposited on the package.

On the other hand, it is possible to determine the above-described influential parameters by the method of this invention in a more reliable manner than before, when it is established beforehand by tests that errors with respect to these influential parameters lead to a characteristic course of the corrected parameters. Thus, it becomes possible to detect in particular:

A change in the denier by adjusting the pump speed 44 and heating 5, by contamination of the spinneret, and by varying the drawoff speed of godet 16;

An absence of filaments, for example, as a result of filament breakage;

An absence of spin finish (consumption of spin finish fluid, breakdown of spin finish application roll 13);

A change in the draw ratio, for example by contamination or abrasion of godets 16, 19.1, 19.2;

A change in physical properties, for example by controlling heating 53; and

Change in takeup speed, for example, by uneven rotation of contact roll 28.

With reference to the illustrated embodiment, it has already been pointed out that the quality signal can be obtained by the combined simultaneous observation of the yarn tension and the package weight, the yarn tension and the yarn tension measured at a different point, the yarn tension and the law of traversing. Further parameters include:

Bulging on the front ends of the package, which may be determined by optical or pneumatic sensing, noise generation and noise analysis, and the package weight.

Shown in FIG. 2 is an embodiment, in which the yarn tension, as is measured between the two draw rolls or godets 19.1 and 19.2, is predetermined as a further parameter. To this end a yarn tensiometer 68 is arranged between the two godets. This yarn tensiometer measures the tension of the yarn advancing in the draw and setting zone. This yarn tension is determined on the one hand by the speed of godets 19.1 and 19.2, moreover, by the effect of heating device 53 in godet 19.1, as well as by further factors. However, not included in this yarn tension is the fluctuation of the yarn tension, which develops as a result of winding and traversing, i.e., when viewed in the yarn path, downstream of godet 19.2. Thus, the measuring of the yarn tension by yarn tensiometer 68 is on the one hand much closer to the origination and processing of the yarn, but on the other hand, it is largely independent of further processing, in particular winding. The courses resulting from yarn tensiometer 68 and yarn tensiometer 8, possibly after suppressing the influences of traversing, are accordingly compared with one another in comparison unit 66. This comparison also allows to find the chronological correlation of courses of critical points, etc. It is possible to detect deviating tendencies of the course, and to determine singular occurrences in the one or the other zone. From all this, is it possible to obtain indications as to the quality, which are especially expressive of the process control as well as the quality of the product.

We claim:

1. A method of processing a continuous synthetic filament material while monitoring its quality, and comprising the steps of performing a production process which includes advancing a continuous synthetic filament material along a path of travel and winding the advancing filament material into a package, monitoring a first parameter which is dependent on the production process or the package and generating a first output signal which is a function of the monitored first parameter, and wherein the first parameter comprises the tension of the advancing material measured at a predetermined location along the advance of the material, monitoring at least a second further parameter which is dependent on the production process or the package and generating a second output signal which is a function of the monitored second parameter, and generating an indication signal whenever the first output signal and at least the second output signal indicate an error typical behavior.

2. The method as defined in claim 1 wherein the generating step includes comparing the first and second output signals simultaneously or chronologically, and generating the indication signal whenever the comparison deviates from a normal value.

3. The method as defined in claim 2 wherein the normal value is defined by an error mask which is stored in a memory.

4. The method as defined in claim 1 wherein the generating step includes interconnecting the first and second outputs, and generating the indication signal whenever the interconnected output signals deviates from a normal value.

5. The method as defined in claim 4 wherein the normal value is defined by an error mask which is stored in a memory.

6. The method as defined in claim 1 wherein the generating step includes determining courses of critical points for each of the first and second signals, comparing the two courses of critical points, and generating the indication signal whenever the compared courses coincide simultaneously or chronologically.

7. The method as defined in claim 1 wherein the second further parameter comprises the tension of the advancing material measured at a location along the advance of the material spaced from said predetermined location.

8. A method of processing a continuous synthetic filament material while monitoring its quality, and comprising the steps of performing a production process which includes advancing a continuous synthetic filament material along a path of travel, gathering the advancing material to form an advancing yarn, winding the advancing yarn into a package, and contacting the advancing yarn with a godet upstream of the winding step, monitoring the yarn tension upstream of the godet and generating a first output signal which is a function of the monitored upstream yarn tension, monitoring the yarn tension downstream of the godet and generating a second output signal which is a function of the monitored downstream yarn tension, and generating an indication signal whenever the first output signal and the second output signal indicate an error typical behavior.

9. A method of producing a continuous synthetic filament material while monitoring its quality, and comprising the steps of performing a production process which includes extruding a thermoplastic material so as to form a plurality of continuous synthetic filaments, advancing the filaments along a path of travel, gathering the advancing material to form an advancing yarn, and then winding the advancing yarn into a package, monitoring a first parameter of the advancing yarn which is dependent on the production process or the package and generating a first output signal which is a function of the monitored first parameter, monitoring a second further parameter of the advancing yarn which is dependent on the production process or the package and generating a second output signal which is a function of the monitored second parameter, and generating an indication signal whenever the first output signal and at least the second output signal indicate an error typical behaviors wherein the step of performing a production process further includes contacting the advancing yarn with a godet upstream of the winding step, and wherein the first parameter comprises the yarn tension upstream of the godet and the second further parameter comprises the yarn tension downstream of the godet.

* * * * *